United States Patent [19]

Filbey et al.

[11] Patent Number: 5,095,765
[45] Date of Patent: Mar. 17, 1992

[54] SAMPLE VALVE FOR STERILE PROCESSING

[75] Inventors: Geoffrey J. Filbey, Weymouth; Richard C. Boulton, Wilmington, both of Mass.

[73] Assignee: Biopure Corporation, Boston, Mass.

[21] Appl. No.: 539,970

[22] Filed: Jun. 15, 1990

[51] Int. Cl.$^5$ .............................................. G01N 1/00
[52] U.S. Cl. .................................................. 73/863.56
[58] Field of Search ........... 73/863.57, 863.71, 863.72, 73/863.81, 863.83–863.86

[56] References Cited

U.S. PATENT DOCUMENTS

| | | |
|---|---|---|
| 2,786,355 | 3/1957 | Day et al. . |
| 3,541,860 | 11/1970 | George . |
| 3,847,022 | 11/1974 | McGinnis . |
| 4,262,534 | 4/1981 | Morrison ........................... 73/863.86 |
| 4,269,064 | 5/1981 | Johnson et al. . |
| 4,423,641 | 1/1984 | Ottung ............................... 73/863.86 |
| 4,594,904 | 6/1986 | Richter .............................. 73/863.86 |
| 4,669,321 | 6/1987 | Meyer . |
| 4,712,434 | 12/1987 | Herwig et al. . |
| 4,744,255 | 3/1988 | Jaeger . |
| 4,887,472 | 12/1989 | Jansen ................................ 73/863.86 |

FOREIGN PATENT DOCUMENTS

| | | | |
|---|---|---|---|
| 2752284 | 6/1978 | Fed. Rep. of Germany ... | 73/863.86 |
| 307302 | 6/1971 | U.S.S.R. ............................ | 73/863.85 |

Primary Examiner—Robert Raevis
Attorney, Agent, or Firm—Hamilton, Brook Smith & Reynolds

[57] ABSTRACT

A valve is disclosed for allowing a sample to be withdrawn from a processing line under sterile conditions. A tip plug is disposed within a bore and is movable between a closed position and an opened position by rotation of a knob. When the tip plug is in the closed position, a sealing land at the tip plug seals a process stream from a sample port, and an annulus disposed about the tip plug provides fluid communication between a flush port and the sample port. A sterilizing fluid is directed between the flush port and the sample port through the annulus for sterilizing the sample port. The valve is opened by moving the tip plug within the bore, whereby the sealing land moves across a sample port orifice defined by the sample port to thereby provide fluid communication between the process stream and the sample port for withdrawal of a sample from the process stream under sterile conditions.

7 Claims, 2 Drawing Sheets

SAMPLE VALVE FOR STERILE PROCESSING

BACKGROUND OF THE INVENTION

Many chemical process streams are operated under sterile conditions; i.e., wherein there is essentially no contamination by microorganisms. However, sterile process streams are often monitored by withdrawing samples of process fluids from those streams. Productivity and product quality can diminish if the process streams are contaminated during sampling.

A common method of withdrawing samples from a sterile process stream includes partitioning the process stream from the environment by a septum. A syringe needle is employed to perforate the septum and to remove a sample from the process stream. Removal of the needle from the septum reseals the process stream. A portion of the withdrawn sample, however, can be trapped within the perforation created by the needle. Reintroduction of the needle at or near a perforation containing remnants of a previous sample can disturb these remnants and cause their reentry into the sterile process stream, thus contaminating otherwise sterile conditions. Septums are also damaged by perforation and can require replacement during processing. Further, pressure within process streams can cause process fluid to leak through perforations in septums, thereby contaminating the septum and the environment.

Conventional valves often trap sample material when they are closed. For example, diaphragm valves typically are closed by directing a diaphragm against an interior surface of the valve. Sample material can become trapped between the diaphragm and the interior surface. Ball valves, as another example, usually include a spherical member having a conduit therethrough which conducts fluid from a process stream when the valve is open. The spherical member is rotated to close the valve, thereby creating a dead space which traps sample material within the conduit. Trapped material within either a diaphragm valve or a ball valve generally cannot be removed without reopening the valve. In addition, a sample side of conventional valves can usually be flushed when the valve is closed only by directing a fluid into the sample side in a direction of flow countercurrent to that of sample flow when the valve is open. Also, fluid is often flushed through separate ports in valves to attempt to sterilize areas where process material has been trapped. This flushing generally is inadequate to remove remnants of previous samples from the sample side of valves.

Thus, a need exists for a new apparatus and method for sampling sterile process streams which minimize or overcome the above-mentioned problems.

SUMMARY OF THE INVENTION

The present invention relates to a valve for withdrawing a process fluid from a process stream under sterile conditions and a method for operating such a valve.

A valve for withdrawing a process fluid from a process stream under sterile conditions includes a valve body having an interior wall defining a bore for receiving the process fluid from the process stream. A tip plug is disposed within the bore and is movable between a closed position and an opened position. A sealing land at the tip plug abuts the interior wall for wiping the interior wall during movement of the tip plug between the closed position and the opened position. A sample port is disposed at the valve body, whereby the sample port is sealed from the process stream by a seal formed between the interior wall and the sealing land when the tip plug is in the closed position. Fluid communication is provided between the process stream and the sample port for withdrawing a process fluid from the process stream under sterile conditions when the tip plug is in the opened position. A flush port is disposed at the valve body for flushing a sterilizing fluid through the bore and the sample port when the tip plug is in the closed position. Flushing means provide fluid communication between the sample port and the flush port when the tip plug is in the closed position.

A method for withdrawing a process fluid from a process stream under sterile conditions includes directing a sterilizing fluid between a flush port and a sample port through a conduit which is defined by a valve body and a tip plug, thereby sterilizing the sample port. The tip plug is moved from a closed position to an opened position within a bore defined by an interior wall within the valve body, thereby providing fluid communication between the process stream and the sample port. The process fluid is directed from the process stream through the sample port under sterile conditions when the tip plug is in the opened position. The tip plug is moved from the opened position to the closed position, whereby a sealing land of the tip plug, which abuts the interior wall and is disposed between the conduit and the process stream, wipes the interior wall. Entrapment of the process fluid between the tip plug and the interior wall is thereby prevented and the process stream is sealed from the sample port. Fluid communication is also provided between the flush port and the sample port for directing a sterilizing fluid between the flush port and the sample port through the conduit.

This invention has many advantages. In general, the valve is flushed with a sterilizing fluid which is conducted through the valve in a direction of flow concurrent with flow of the sampled material. Also, dead spaces are not formed by movement of the tip plug between the closed and opened positions. Further, the tip plug is located proximate to the current of process flow within the process stream, thereby substantially preventing formation of dead space or eddies within the process stream where process materials could become trapped. The sealing land at the tip plug wipes the interior wall of the valve during movement of the tip plug between the closed and opened positions, thereby preventing entrapment of any portion of the process stream by the tip plug. Absence of either dead space or of trapped process fluid within the valve substantially reduces the possibility that the sterile process stream or samples withdrawn from the process stream will be contaminated by remnants of previously sampled process fluid.

DETAILED DESCRIPTION OF THE DRAWINGS

DETAILED DESCRIPTION OF THE INVENTION

The features and other details of the invention will now be more particularly described with reference to the accompanying drawings and pointed out in the claims. It will be understood that the particular embodiments of the invention are shown by way of illustration and not as a limitation of the invention. The principle features of the invention may be employed in various embodiments without departing from the scope of the invention.

Figure 1:
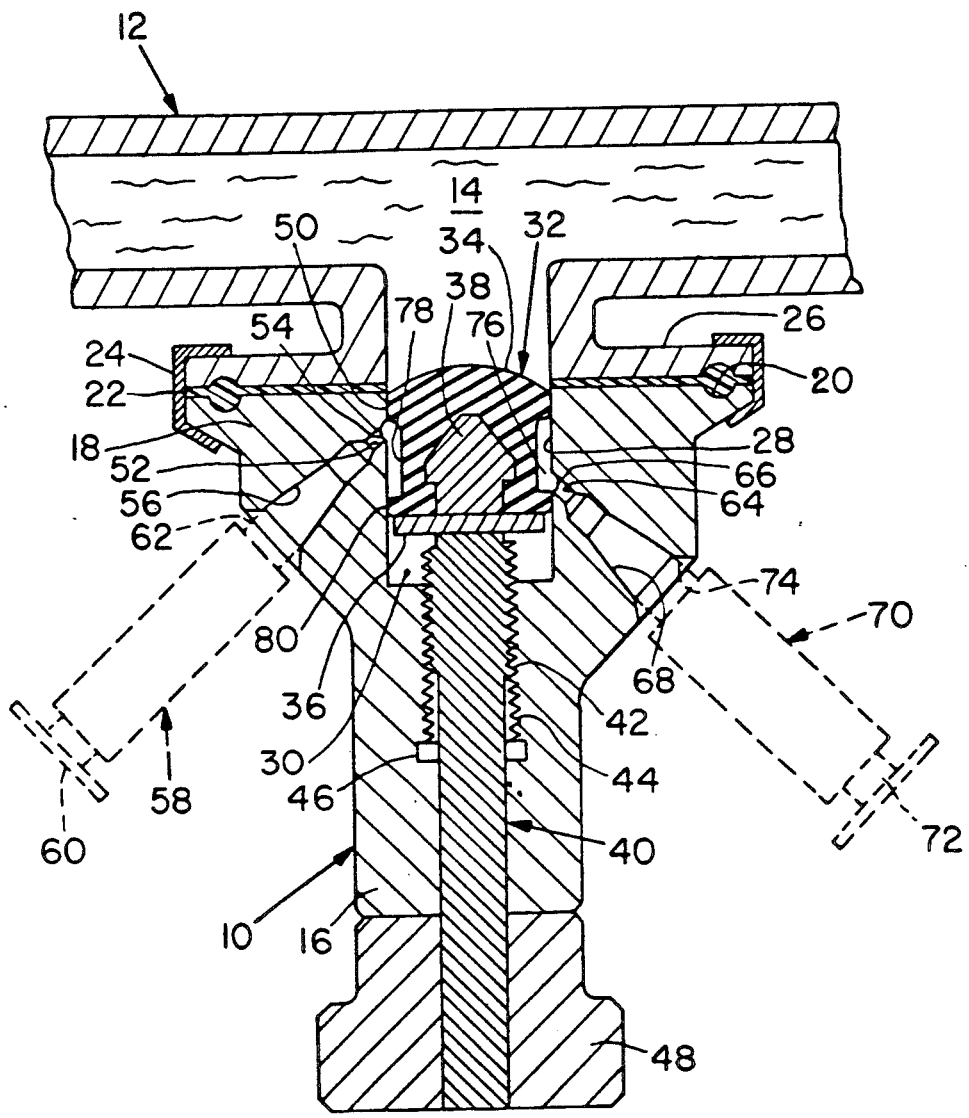
FIG. 1 is a section view of one embodiment of the valve of the present invention wherein a tip plug is in a closed position.

As shown in FIG. 1, valve 10 is disposed at a point in a process stream 12 from which process fluid 14 is to be withdrawn. Suitable process streams include those which are sterile, i.e. essentially no microbial life forms are present, and wherein sterile conditions within process stream 12 must be maintained during withdrawal of process fluid 14 from process stream 12. It is to be understood, however, that valve 10 can withdraw process fluids under conditions which are not sterile.

Valve 10 has a valve body 16. Clamp flange 18 extends radially from valve body 16. Sanitary gasket groove 20 extends within clamp flange 18 for receiving sanitary gasket 22. Sanitary gasket 22 is preferably formed of a suitable material for contact with process fluid 14. Examples of suitable materials include Buna N ®, Viton ® and Ethyldipropylmethane (EDPM). Clamp 24 secures clamp flange 18 to fitting 26 at process stream 12.

Valve body 16 includes interior wall 28 which defines a bore 30 extending through valve body 16. In a preferred embodiment, valve body 16 is formed of stainless steel, such as 316L stainless steel. However, other materials can be used which are sufficiently resistant to fracture and are suitable for sterile-use applications, including, for example, high-density polyurethane. In a preferred embodiment, valve body 16 is machined from solid round stock (R-stock) 316L stainless steel.

Bore 30 can be machined from the round stock and then smoothed to obtain interior wall 28. Interior wall 28 preferably has a dimensional tolerance of less than about 0.002 inches. Interior wall 28 is sufficiently smooth to form a seal between bore 30 and tip plug 32. Interior wall 28 can be sufficiently smoothed using, for example, 400 grit sandpaper. In addition, interior wall 28 can be polished by a suitable method, such as by applying a lapping compound or by electropolishing, wherein a small amount of metal at interior wall 28 is removed by submerging interior wall 28 in a salt solution and connecting it to an electric current so that the surface of interior wall 28 operates as an anode.

Tip plug 32 is disposed within bore 30 and can be formed of a suitable material for exposure to process fluid 14. Tip plug 32 can be formed by pour molding, wherein a monomer or polymer, which has been poured within a mold is substantially polymerized in the presence of an activator. A preferred material for manufacture of tip plug 32 by pour molding is RTV "J" Silicone, commerically available from Dow Corning. Alternatively, tip plug 32 can be formed by injection molding of a suitable thermoplastic or thermoset. Tip plug 32 is sufficiently resilient to allow pressure at a pressure surface 34 of tip plug 32 to deform tip plug 32 outwardly against interior wall 28. In a preferred embodiment, the durometer hardness of tip plug 32 is about 60, Shore A.

Tip plug 32 is seated on plug seating flange 36 and is secured by a plug lock 38 to a valve stem 40. Movement of valve stem 40 directs movement of tip plug 32 within bore 30. In a preferred embodiment, valve stem threads 42 at valve stem 40 are movable along valve body threads 44 within valve body 16 for movement of valve stem 40 and of tip plug 32 within bore 30. Valve body threads 44 terminate within valve body 16 at thread relief 46. Manual rotation of knob 48, which is fixed to valve stem 40, causes movement of valve stem 40 within valve body 16. Alternatively, movement of valve stem 40 within bore 30 can be automated, such as by actuation of a pneumatic cylinder, not shown, fixed to valve stem 40, whereby valve stem 40 is directed within bore 30 without rotation, or with rotation using an electric motor, also not shown.

Sealing land 50 at tip plug 32 abuts interior wall 28. The diameter of tip plug 32 at sealing land 50 is sufficient to form a seal at sealing land 50 and interior wall 28 which prevents passage of process fluid 14 across sealing land 50 when tip plug 32 is in the closed position. Tip plug 32 is dimensioned and configured to form an interference fit with bore 30 at sealing land 50. Movement of tip plug 32 within bore 30 causes sealing land 50 to wipe interior wall 28.

Sample port 52 is located at valve body 16 and defines sample port orifice 54. Sample port 52 can include a fitting which is suitable for supporting a receptacle for receiving process fluid 14 from process stream 12. In a preferred embodiment, the fitting is a taper fitting 56 and the receptacle is a suitable sample port syringe 58, shown in phantom. An example of suitable sample port syringe 58 is a conventional syringe having a plunger 60 and a taper 62. Taper fitting 56 is dimensioned and configured for providing a seal between taper fitting 56 and taper 62. Sample port orifice 54 is sealed from process stream 12 by a seal formed between sealing land 50 and interior wall 28 when tip plug 32 is in the closed position.

Flush port 64 is located at valve body 16 and defines a flush port orifice 66. Flush port 64 can include a fitting which is suitable for supporting a receptacle for delivering a sterilizing fluid to bore 30. Flush port 64 is located along bore 30 at a point distal from the path of sealing land 50 within bore 30, such that process fluid 14 is sealed from flush port 64 by sealing land 50 when sample port 52 is receiving process fluid 14 from process stream 12. In a preferred embodiment, the fitting is a taper fitting 68 and the receptacle is a suitable flush port syringe 70, shown in phantom. An example of a suitable flush port syringe 70 is a conventional syringe having a flush port plunger 72 and a taper 74. Taper fitting 68 is dimensioned and configured to provide a seal between taper fitting 68 and taper 74. Flush port orifice 66 provides fluid communication between bore 30 and flush port syringe 70.

Flushing means for providing fluid communication between sample port 52 and flush port 64 when tip plug 2 is in the closed position includes a conduit within bore 30 defined by interior wall 28 and tip plug 32 which extends between sample port 52 and flush port 64. In a preferred embodiment, the conduit comprises annulus 76 which is defined by interior wall 28 and recessed portion 78 extending about tip plug 32. Sealing land 50 and interior wall 28 provide a seal between process stream and annulus 76. A seal is also provided between interior sealing land 80 and interior wall 28 for preventing flow of fluid from annulus 76 to valve stem 40.

Figure 2:
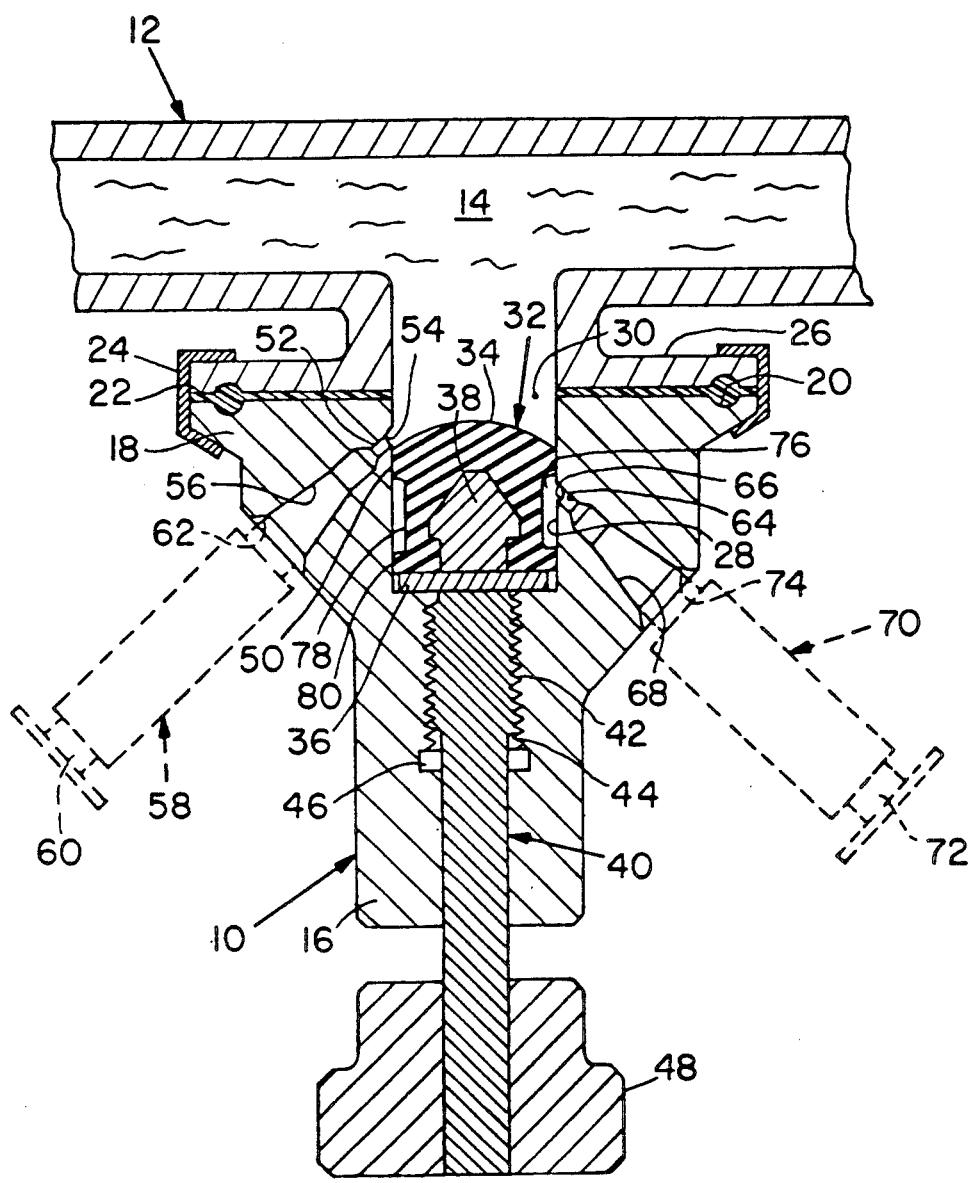
FIG. 2 is a section view of the embodiment of FIG. 1 wherein the tip plug is in an opened position.

Tip plug 32 is movable from the closed position, shown in FIG. 1, to an opened position, shown in FIG. 2. Tip plug 32 is moved from the closed position to the opened position by manually rotating knob 48. Rotation of knob 48 rotates valve stem 40. As valve stem 40 is rotated, valve stem threads 42 are guided along valve body threads 44 for movement of valve stem 40 along a major axis of valve stem 40 to thereby direct tip plug 32 from the closed position to the opened position.

As tip plug 32 is directed from the closed position to the opened position by rotation of knob 40, sealing land 50 wipes interior wall 28 and moves across sample port orifice 54. Continued movement of tip plug 32 provides fluid communication between sample port orifice 52 and process stream 12 for withdrawal of at least a portion of process fluid 14 from process stream 12 through sample port 52. Sample port syringe 58 collects at least a portion of process fluid 14 at sample port 52. Pressure within process stream 12 can direct process fluid from process stream through sample port orifice 54 and into sample port syringe 58. Alternatively, vacuum can be applied at sample port 52 to withdraw at least a portion of process fluid, such as by withdrawing sample port syringe plunger 60 of sample port syringe 58.

After at least a portion of process fluid 14 has been withdrawn from process stream 12, tip plug 32 can be moved from the opened position to the closed position by rotation of knob 48 and valve stem 40 in a direction opposite to that by which tip plug 32 was moved from the closed position to the opened position, as described above. As tip plug 32 moves from the opened position to the closed position, sealing land 50 wipes interior wall 28 such as to direct process fluid 14 along interior wall 28, thereby preventing entrapment of process fluid 14, or components of process fluid 14, between sealing land 50 and interior wall 28. Sealing land 50 moves across sample port orifice as tip plug is directed from the opened position to the closed position. When tip plug 32 has returned to the closed position, sample port 52 is sealed from process stream 12 by the seal formed between sealing land 50 and interior wall 28. Fluid communication between sample port 52 and flush port 64 is also provided by establishing fluid communication between sample port 52 and annulus 76 as sealing land 50 moves across sample port orifice 54 toward the closed position of tip plug 32.

Sample port 52 can be sterilized by directing a sterilizing fluid from flush port syringe 70 at flush port 64 through annulus 76 and from annulus 76 through sample port orifice 54 when tip plug 32 is in the closed position. Flow of sterilizing fluid through annulus 76 is restricted by interior seal 80 and by sealing land 50, thereby preventing flow of sterilizing fluid from annulus 76 to valve stem 42 or into process stream 12. Remnants of process fluid 14 at sample port orifice 54 are thereby flushed from sample port orifice 54 in a direction of flow generally concurrent with the direction of flow of samples taken through sample port 52 when tip plug 32 is in the opened position. Sterilizing fluid can also be directed from sample port 52 through annulus 76 and from annulus 76 through flush port 64 for flushing of sample port 52 in a direction of flow countercurrent to that of samples taken through sample port 52.

A method for withdrawing at least a portion of process fluid 14 from process stream 12 under sterile conditions includes directing a sufficient amount of sterilizing fluid to fill annulus 76 from sample port syringe 58 through annulus 76 into flush port syringe 70 by withdrawing flush port syringe plunger 72. A sterilizing fluid is then directed from flush port syringe 70 through annulus 76 and sample port orifice 54 into the sample port syringe 58 by withdrawing sample port syringe plunger 60. The sterilizing fluid is spent upon contact with organic material of process fluid 14. Sample port syringe 58 containing spent sterilizing fluid is then removed and is replaced with a second sample port syringe 58, containing a fresh sterilizing fluid. Sterilizing fluid within sample port syringe 58 is then directed from sample port syringe 58 by withdrawing the flush port syringe plunger 72, thereby directing the sterilizing fluid solution through sample port orifice 54 and annulus 76 into the flush port syringe 70. Flush port syringe 70, containing spent sterilizing fluid, is then removed from taper fitting 68 and discarded. Sample port syringe 58 is removed from luer taper fitting 56 and replaced with a second sterile, empty sample port syringe 58.

The sterilizing fluid can be a fluid which is capable of substantially sterilizing surfaces of valve body 10 and tip plug 32 contacted by organic material. An example of a suitable sterilizing fluid for use with the present invention comprises 0.5 molar caustic solution. The sterilizing fluid can be delivered through flush port orifice 66, bore 30 and sample port orifice 54 through a closed recirculating loop, not shown. It is to be understood, however, that other sterilizing means can be used, such as steam delivered through flush port orifice 66 under conditions sufficient to sterilize bore 30 and sample port 52, i.e. saturated steam at a pressure greater than about 15 psig. Another example of a sterilizing and sampling system includes an automated system of piping or tubing, not shown, which is fitted to sample port orifice 54 and flush port orifice 66 as an alternative to manually operated sampling and flushing devices.

Valve 10 is then opened by manually rotating knob 50, thereby moving tip plug 32 from the closed position to the opened position. Sealing land 50 wipes interior wall 28 and moves across sample port orifice 54 to provide fluid communication between process stream 12 and sample port 52. Pressure within process stream 12 directs process fluid 14 from process stream 12 through sample port orifice 54. At least a portion of process fluid 14 from process stream 12 is thereby directed from process stream 12 through sample port orifice 54 into sample port syringe 58. Alternatively, sample port syringe plunger 60 can be withdrawn to direct at least a portion of process fluid 14 from process stream 12 into sample port syringe 58.

Valve 10 is then closed by rotating knob 48 in a direction opposite to that by which valve 10 was opened, thereby moving tip plug 32 from the opened position to the closed position. Sealing land 50 wipes interior wall 28 during movement of tip plug 32 for directing material at interior wall 28 toward process stream 12. Sealing land 50 moves across sample port orifice 54, thereby securing flow from process stream 12 through sample port 52. Sample port syringe 58, containing process fluid 14 from process stream 12 and a trace amount of sterilizing fluid, is removed and discarded.

A second sterile, empty sample port syringe 58 is then fitted to luer taper fitting 56 at sample port 52 and valve 10 is opened again for directing at least a portion of process fluid 14 from the process stream 12 into sample port syringe 58 under sterile conditions. Valve 10 is closed after process fluid 14 has been collected within sample port syringe 58 to form a sample. Sample port syringe 58 is then removed from sample port 52 and the sample contained within the sample port syringe 58 is sealed by a suitable means.

Valve 10 is then sterilized by fitting a sterile, empty sample port syringe 58 to luer taper fitting 56 of sample port 52. Flush port syringe 70, containing a measured volume of sterilizing fluid, is fitted to luer taper fitting 62 of flush port 64. Sample port syringe plunger 72 is inserted into flush part syringe 70 to direct sterilizing fluid from flush port syringe 70 through annulus 76 and into sample port syringe 58. When flush port syringe 70 is empty, it is removed and replaced with a second flush port syringe 70. Flush port syringe plunger 72 is then withdrawn to direct about one-half of the sterilizing fluid in sample port syringe 58 through sample port orifice 54 and annulus 76 into flush port syringe 70. Sample port syringe 58 and flush port syringe 70 are left in place until a subsequent sample is to be withdrawn.

To withdraw another sample, the remainder of sterilizing fluid in flush port syringe 70 is directed through annulus 76 and sample port orifice 54 into the sample port syringe 58. Sample port syringe 58 is removed and replaced with a sterile sample port syringe 58 containing a volume of sterilizing fluid sufficient to fill annulus 76. The sterilizing fluid is directed from the sample port syringe 58 through sample port orifice 54 and annulus 76 into flush port syringe 70. Sample port 52 is flushed with material from process stream 12 by opening and then closing valve 10. Sample port syringe 58 is removed and replaced with a sterile, empty sample port syringe 58 for collecting a sample from process stream 12. Samples can thereby be taken from process stream 12 under sterile conditions without contaminating process stream 12 and without contamination of samples with remnants of previous samples.

Valve 10 is suitable for withdrawal of samples from process streams which are sterile and from process streams which are not sterile. Valve 10 can also be employed to control process streams by directing the path of processing through sample port 52.

Equivalents

Those skilled in the art will recognize or be able to ascertain using no more than routine experimentation, many equivalents to the specific embodiments of the invention described specifically herein. Such equivalents are intended to be encompassed in the scope of the following claims.

We claim:

1. A valve for withdrawing a process fluid from a process stream under sterile conditions comprising:
   a) a valve body including an interior wall defining a bore for receiving the process fluid from the process stream;
   b) a tip plug disposed within the bore and movable between a closed position and an opened position;
   c) a sealing land at the tip plug abutting the interior wall for wiping said interior wall during movement of the tip plug between the closed position and the opened position;
   d) a sample port disposed at the valve body, whereby the sample port is sealed from the process stream by a seal formed between the interior wall and the sealing land when the tip plug is in the closed position and whereby fluid communication is provided between the process stream and the sample port for withdrawing a process fluid from the process stream when the tip plug is in the opened position;
   e) a flush port disposed at the valve body for flushing a sterilizing fluid through the bore and the sample port when the tip plug is in the closed position, the flush port being sealed from the sample port by the sealing land when the tip plug is in the opened position; and
   f) flushing means for providing fluid communication between the sample port and the flush port when the tip plug is in the closed position.

2. A valve of claim 1 wherein the tip plug further includes a recessed portion, whereby the recessed portion and the interior wall define an annulus extending about the tip plug which provides fluid communication between the sample port and the flush port when the tip plug is in the closed position.

3. A valve of claim 2 wherein the tip plug is formed of a resilient material and wherein the tip plug further includes a pressure surface for exposure to the process stream, whereby the process stream applies pressure to the pressure surface, thereby deforming the tip plug such that the sealing land is directed against the interior wall to form a seal at the sealing land between the pressure surface and the annulus.

4. A valve of claim 3 further including a knob and a valve stem connecting the knob and the tip plug, whereby the tip plug is directed between the closed position and the opened position by rotation of the knob.

5. A valve of claim 4 wherein the valve stem is threaded for movement within the valve body, whereby rotation of the knob directs the tip plug between the closed position and the opened position.

6. A valve of claim 5 wherein the tip plug comprises silicone.

7. A method for withdrawing a process fluid from a process stream under sterile conditions comprising the step of:
   a) directing a sterilizing fluid between a flush port and a sample port through a passageway which is defined by a valve body and a tip plug, thereby sterilizing the sample port;
   b) moving the tip plug from a closed position to an opened position within a bore defined by an interior wall within the valve body, whereby a sealing land at the tip plug seals the sample port from the flush port, the sealing land abutting the interior wall and disposed between the sample port and the flush port, the opened position of the tip plug providing fluid communication between the process stream and the sample port;
   c) directing the process fluid from the process stream through the sample port under sterile conditions when the tip plug is in the opened position; and
   d) moving the tip plug from the opened position to the closed position, whereby the sealing land wipes the interior wall, thereby preventing entrapment of the process fluid between the tip plug and the interior wall and sealing the process stream from the sample port, and whereby fluid communication is provided between the flush port and the sample port for directing a sterilizing fluid between the flush port and the sample port through the passageway.

* * * * *